US012612589B2

(12) United States Patent
Sasserath et al.

(10) Patent No.: US 12,612,589 B2
(45) Date of Patent: Apr. 28, 2026

(54) INTEGRATED WASTE REMOVAL SYSTEM FOR CELL CULTURE BIOREACTOR

(71) Applicant: Sciperio, Inc, Orlando, FL (US)

(72) Inventors: Trevor Sasserath, Orlando, FL (US); Janice M. Moser, Oviedo, FL (US); Casey W. Perkowski, Winter Park, FL (US); Pierce J. Busse, Pensacola, FL (US); Kelly Haupfear, Titusville, FL (US); Kenneth H. Church, Orlando, FL (US)

(73) Assignee: Sciperio, Inc, Orlando, FL (US)

( * ) Notice: Subject to any disclaimer, the term of this patent is extended or adjusted under 35 U.S.C. 154(b) by 516 days.

(21) Appl. No.: 18/304,271

(22) Filed: Apr. 20, 2023

(65) Prior Publication Data

US 2023/0357697 A1     Nov. 9, 2023

Related U.S. Application Data

(60) Provisional application No. 63/339,140, filed on May 6, 2022.

(51) Int. Cl.
*C12M 1/00*       (2006.01)
*C12M 1/06*       (2006.01)
(Continued)

(52) U.S. Cl.
CPC .............. *C12M 39/00* (2013.01); *C12M 1/06* (2013.01); *C12M 23/16* (2013.01); *C12M 29/18* (2013.01); *C12M 41/16* (2013.01)

(58) Field of Classification Search
CPC ........ C12M 39/00; C12M 1/06; C12M 23/16; C12M 29/18; C12M 29/26; C12M 41/16; C12M 41/26; C12M 41/48; C12M 47/02
See application file for complete search history.

(56) References Cited

U.S. PATENT DOCUMENTS

| | | | |
|---|---|---|---|
| 4,370,234 A | 1/1983 | Marsland | |
| 2006/0019385 A1* | 1/2006 | Smith .................... | C12M 29/16 |
| | | | 435/348 |

(Continued)

FOREIGN PATENT DOCUMENTS

| | | | |
|---|---|---|---|
| CA | 2009761 A1 | 8/1990 | |
| EP | 0488665 A1 | 6/1992 | |
| WO | WO-0046354 A1 * | 8/2000 | ............ C12M 41/32 |

*Primary Examiner* — Michael L Hobbs
(74) *Attorney, Agent, or Firm* — Goodhue, Coleman & Owens, P.C.

(57)         ABSTRACT

A method includes directing fluid flow from a bioreactor to an external path of a re-circulation loop, separating cells from the medium and returning the cells to the bioreactor thereby leaving spent medium, depleting the spent medium of biological waste products, replenishing the spent medium with beneficial growth factors to thereby provide replenished medium, and directing the replenished medium back to the bioreactor to thereby complete the re-circulation loop such that recycling of the medium occurs. The replenishing of the spent medium with beneficial growth factors may occur within a medium collection reservoir. The method may further include monitoring the spent medium within the medium collection reservoir including temperature of the spent medium within the medium collection reservoir and pH of the spent medium within the medium collection reservoir.

17 Claims, 4 Drawing Sheets

(51) Int. Cl.
  *C12M 1/34*    (2006.01)
  *C12M 3/06*    (2006.01)

(56)       References Cited

U.S. PATENT DOCUMENTS

| | | | |
|---|---|---|---|
| 2022/0186173 A1* | 6/2022 | Liu | C12M 47/02 |
| 2024/0218311 A1* | 7/2024 | Nahmias | C12N 5/0634 |
| 2025/0163356 A1* | 5/2025 | Nahmias | C12M 29/18 |

* cited by examiner

1

INTEGRATED WASTE REMOVAL SYSTEM FOR CELL CULTURE BIOREACTOR

RELATED APPLICATIONS

This application claims priority to U.S. provisional patent application No. 63/339,140, filed May 6, 2022, entitled "Integrated waste removal system for cell culture bioreactor", hereby incorporated by reference in its entirety.

FEDERAL SPONSORHSIP

This invention was made with government support under HU0001-20-2-0011 awarded by the Department of Defense. The government has certain rights in the invention.

FIELD OF THE INVENTION

The present invention relates to cell culture bioreactors. More particularly, but not exclusively, the present invention relates to an integrated waste removal system for cell culture bioreactors.

BACKGROUND

In recent years, cell culture bioreactors have been employed in the mass production of biologics, both in the mass-production of cells for cellular therapies and for biological derivatives. Traditional bioreactors utilize an array of sensors and controllers to maintain precise control over environmental conditions, however a primary concern when it comes to long-term bioreactor cell culture is the accumulation of cellular waste products in the culture medium. Regardless of the end product being manufactured, all cells produce cytotoxic waste products as a byproduct of metabolism, such as ammonia and lactate, that can impair the ability of the cells to proliferate and grow efficiently.

Current, standard methods of cell culture involve the manual removal of culture medium from the reactor and replacement with fresh medium to remove waste products and replenish any consumed factors. This can prove to be problematic in situations where medium costs are high or in settings where exposing the contents of the reactor to a non-sterile environment would compromise culture integrity.

What is needed are methods and systems which provide for waste removal from cell culture bioreactors which does not require manual removal of the culture medium from the reactor.

SUMMARY

Therefore, it is a primary object, feature, or advantage of the present invention to improve over the state of the art.

It is a further object, feature, or advantage of the present invention to provide an in-line medium filtration for waste byproduct removal that is incorporated into a bioreactor.

It is a still further object, feature, or advantage of the present invention to provide for an in-line medium filtration for waste byproduct removal that is incorporated into a bioreactor which diverts spend medium into an external flow path for processing.

Another object, feature, or advantage is to provide an in-line medium filtration for waste byproduct removal that is incorporated into a bioreactor to deplete spent medium of biological waste products using ion-exchange resins.

Yet another object, feature, or advantage is to provide an in-line medium filtration for waste byproduct removal that is incorporated into a bioreactor which replenishes depleted medium with beneficial growth factors.

A further object, feature, or advantage is to provide an automated system for controlling a bioreactor and associated waste byproduct removal processes, and replenishment processes.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by any objects, features, or advantages stated herein.

An in-line medium filtration system that removes metabolic waste products without requiring culture media exchanges that is incorporated into a bioreactor using an automated, media recirculation loop. The in-line medium filtration system will remove cytotoxic byproducts of cellular metabolism, such as lactate and ammonia, and prevent interference with cell proliferation and differentiation. Removal of cytotoxic waste will increase cell health and downstream yields, while reducing medium costs.

According to one aspect, a method includes directing fluid flow from a bioreactor to an external path of a re-circulation loop, separating cells from the medium and returning the cells to the bioreactor thereby leaving spent medium, depleting the spent medium of biological waste products, replenishing the spent medium with beneficial growth factors to thereby provide replenished medium, and directing the replenished medium back to the bioreactor to thereby complete the re-circulation loop such that recycling of the medium occurs. The replenishing of the spent medium with beneficial growth factors may occur within a medium collection reservoir. The method may further include monitoring the spent medium within the medium collection reservoir including temperature of the spent medium within the medium collection reservoir and pH of the spent medium within the medium collection reservoir. A control system may receive data generated from the monitoring the spent medium within the medium collection reservoir and the control system may determines quantities of the beneficial growth factor to add to the medium collection reservoir. The step of depleting the spent medium of biological waste products may be performed using one or more ion-exchange resins. The step of separating the cells from the medium may be performed using a separation system comprising at least one of filters and a microfluidic device. The control system may provide for controlling the directing fluid flow from the bioreactor to the external path of the re-circulation loop. The separating of the cells may be performed in-line.

According to another aspect, a system includes a bioreactor comprising a reaction chamber, an agitation system with an impeller, an output line and a return line, an in-line separation system to separate cells from medium fluidly connected to the output line from the bioreactor to thereby leave spent medium, a biological waste removal system for depleting the spent medium of biological waste materials, and a medium collection reservoir fluidly connected to an output from the plurality of ion-exchange resins. The bioreactor, in-line separation system, biological waste removal system, and medium collection reservoir may be arranged to provide a self-contained closed-system recirculation loop. The system may further include a control system for monitoring and/or control of the system. The system may further include a first plurality of sensors associated with the bioreactor and operatively connected to the control system and a second plurality of sensors associated with the medium collection reservoir and operatively connected to the control system. The in-line separation system may include filters and/or microfluidic devices. The biological waste removal system may include a plurality of ion-exchange resins. The medium collection reservoir may include an agitation system with an impeller.

BRIEF DESCRIPTION OF THE DRAWINGS

Illustrated embodiments of the disclosure are described in detail below with reference to the attached drawing figures, which are incorporated by reference herein.

DETAILED DESCRIPTION

The present disclosure describes methods and systems for an in-line medium filtration for waste byproduct removal that is incorporated into a bioreactor comprised of a self-contained closed-system recirculation loop. The self-contained closed-system recirculation loop may provide for diverting spent medium into an external flow path for processing, depleting spent medium of biological waste products using ion-exchange resins, and replenishing depleted medium with beneficial growth factors.

Figure 1:
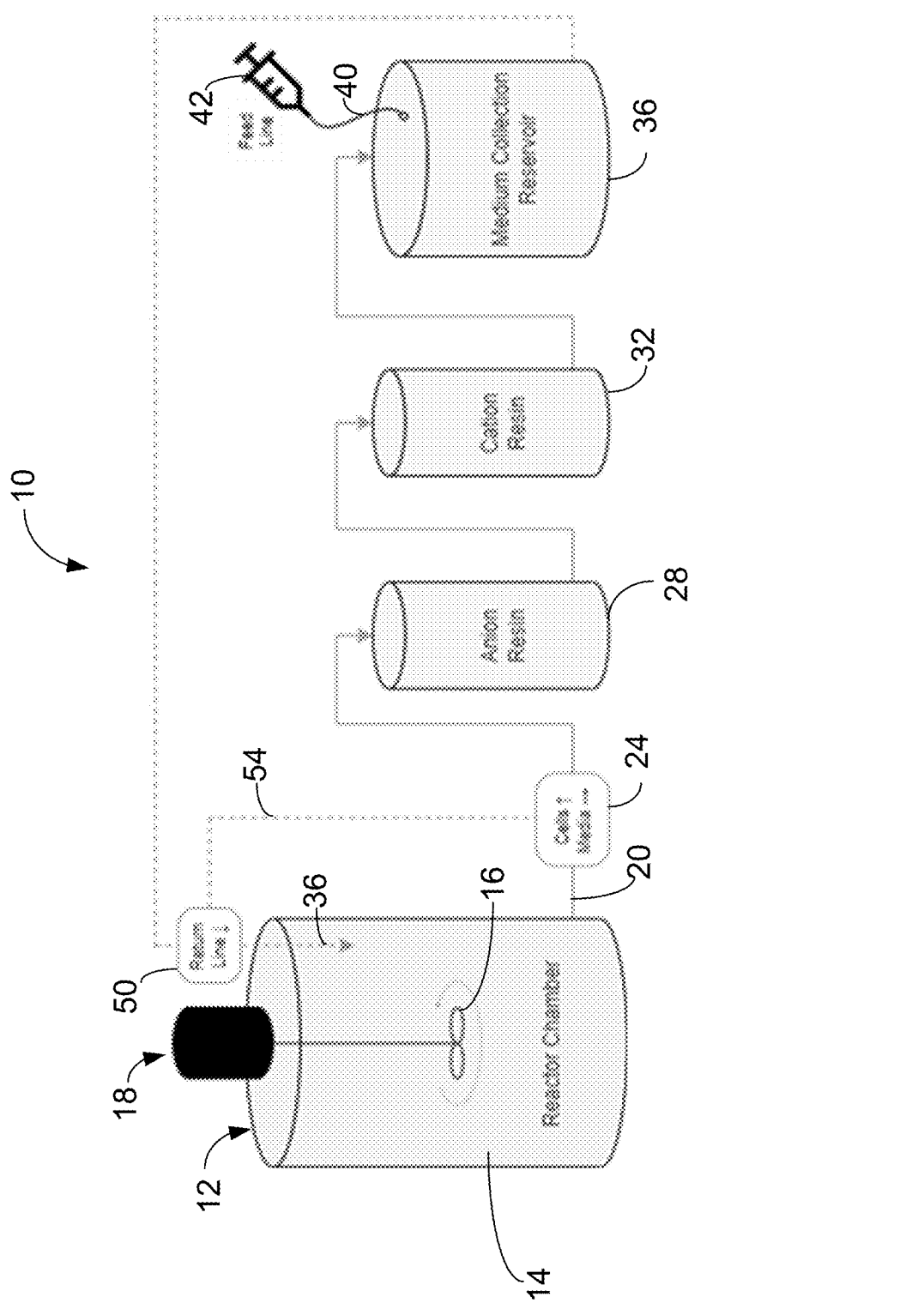
FIG. 1 is an autonomously operated stirred-tank bioreactor with integrated waste-depletion circulation loop.

FIG. 1 provides a pictorial representation of one example of a system 10. The system 10 includes a bioreactor 12. The bioreactor 12 is a stirred-tank bioreactor. It includes a single, isolated reaction chamber 14 as shown. An impeller 16 is shown as a part of an agitation system 18. There is an output line 20 shown. Fluid flow through the output line 20 may be controlled through appropriate use of one or more valves and one or more pumps (not shown). Fluid containing cells and medium to a separation system 24. The separation system 24 is configured to separate cells from the medium. This may be achieved in a variety of ways depending on the cells, the media, desired operating conditions, and other factors. Examples of separation systems 24 include filters such as tangential flow filters, microfluidics, or other separation mediums. After separation, cells may be directed along fluid path 54 to a return line 50 which is fluidly connected to the reaction chamber 14. After separation from the cells, the medium may be diverted through a tertiary flow path in order to deplete the spent medium of biological waste products such as through using ion-exchange resins. For example, a series of ion-exchange resins such as an anion resin 28 and a cation resin 32 may be used.

Ion-exchange resins have been demonstrated to be effective in minimizing levels of toxic chemicals in landfill wastewater runoff. These ion-exchange surfaces utilize charge-charge interactions to remove polar compounds from aqueous solutions, including metals and inhibitory byproducts of cell culture, such as ammonia and lactate. Previous studies have been conducted on the practicality of using ion-exchange resins and membranes in the context of binding excess metals and waste products of cell culture. However, here such technology is incorporated into an impeller-driven closed-system bioreactor with a recirculation component. Also note here that recirculating cells are separated and waste products are removed without necessitating partial or complete medium exchanges.

After the spent medium has had biological waste products removed through the ion-exchange resins or otherwise, the spent medium is directed to a medium collection reservoir 36. Beneficial factors have been removed from culture medium as both a normal byproduct of cell culture, and as a side effect of exposure to ion-exchange resins. After the media has been diverted through both ion-exchange resin cartridges, it accumulates in the medium collection reservoir 36 which is a secondary collection reservoir. Medium in this reservoir 36 is adjusted back to optimal conditions through targeted component delivery. Targeted supplementation can be achieved with any fluidic handling method, such as syringe pumps, peristaltic pumps, micropipettes, or other similar methods of low-volume (<10 mL) fluid handling. A feedline 40 is shown along with one or more components 42. Medium adjustment may be performed in an automated manner, based on previously calculated metabolic and synthetic depletion rates, as well as real-time feedback obtained from an array of biosensors. Adjusted parameters include, but are not limited to, pH, temperature, osmolality, and growth factor concentration. After replenishment, the medium is pumped back into the reaction chamber 14 through the return line 50 to continue the cell culture process.

Figure 2:
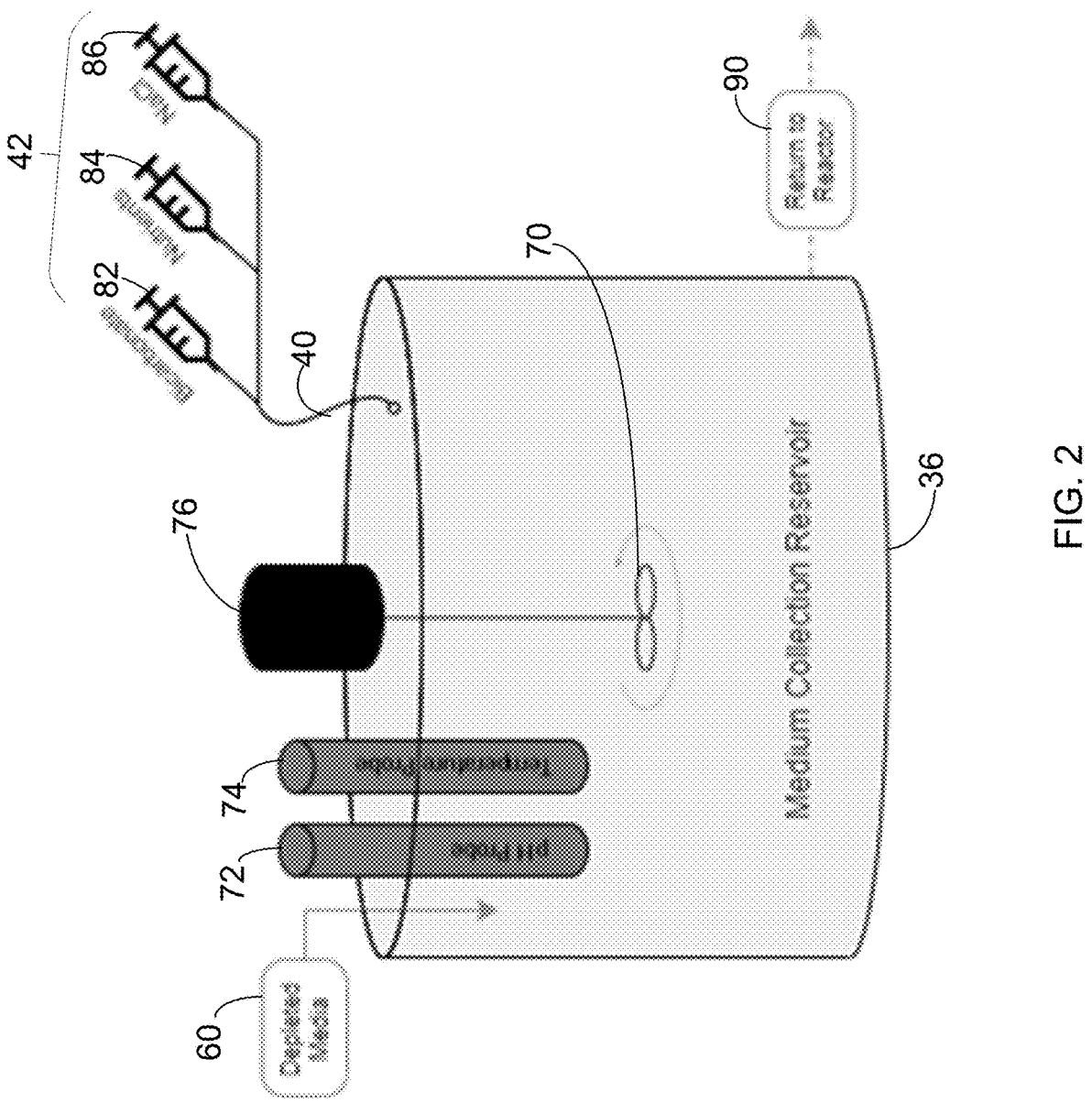
FIG. 2 is a diagram showing sensors in collection reservoir and methods of nutrient delivery.

FIG. 2 illustrates the medium collection reservoir 36 in more detail. As previously explained, depleted or spent media 60 enters the medium collection reservoir 36. An array of different biosensors may be present such as a pH probes 72, temperature sensors 74, or other types of sensors. Data from sensors 72, 74 may be used by a control system. The medium collection reservoir 36 also has an impeller 70 as a part of an agitation system 76. An input line 40 allows for medium replenishment through a component delivery system 42 that may provide for adding one or more components such as bicarbonate input 82, nutrients input 84, and NaCl input 86. Other types of inputs may be present as a part of the component delivery system 42. The medium reservoir 36 may have one or more outputs such as may be controlled by valves, pumps, or other actuators to return replenished medium to the bioreactor through a fluid line 90.

Figure 3:
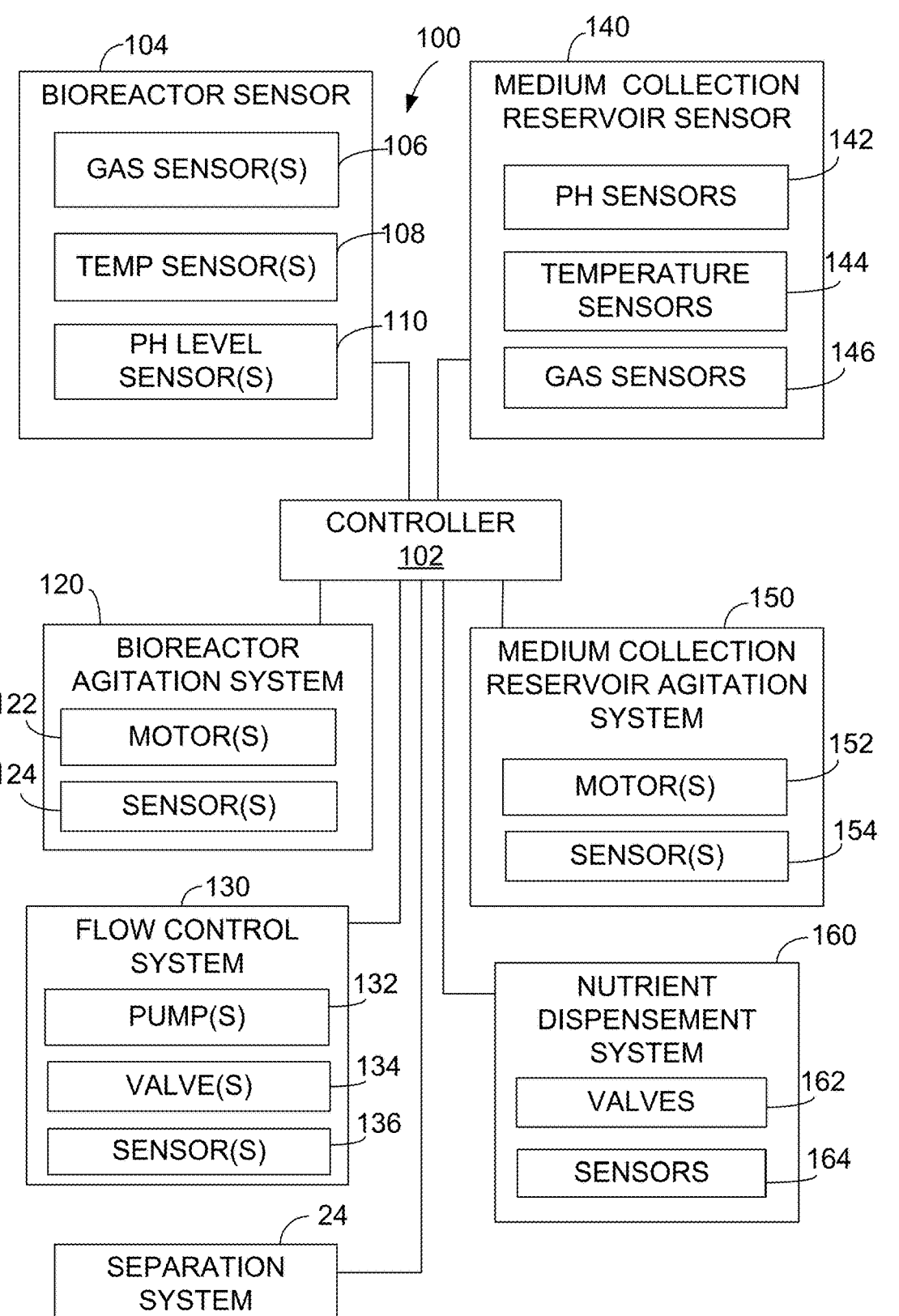
FIG. 3 is a block diagram illustrating one example of a control system.

FIG. 3 is a block diagram illustrating one example of a control system 100. The control system 100 may be used monitor and/or control at least one of the bioreactor and the medium collection reservoir. A controller 102 is shown which may be a computing device such as a microcontroller, processor, an integrated circuit, or other type of intelligent control. The controller 102 need not be a single intelligent control but may include multiple intelligent controls which are networked, share a common, interface, or otherwise communicate. A plurality of bioreactor sensors 104 are shown which are electrically connected to the controller 102. This may include gas sensors 106, temperature sensors 108, and pH Level sensors 110. Of course, any number of other types of sensors may be present as may be useful in monitoring a bioreactor. An agitation system 120 is shown which may include one or more motors 122 and one or more sensors 124 electrically connected to the controller. The agitation system 120 may be an impeller-driven agitation system. Flow control systems 130 are also shown which are electrically connected to the controller 102. The flow control systems may include one or more pumps 132, one or more valves 134, and one or more sensors 136 which may be used to control fluid flow throughout the re-circulating system. Thus, the controller 102 may be used to determine when to release medium from the bioreactor, when to release medium from the medium collection reservoir, or when to perform other the flow-related functions.

The separation system 24 is also shown which may be electrically connected to the controller 102. In some embodiments, the separation system 24 may include sensors indicative of status or progress of the separation system 24 or the ability to control settings or functionality of the separation system 24.

A plurality of medium collection reservoir sensors 140 are shown which are electrically connected to the controller 102. This may include pH sensors 142, temperature sensors 144, gas sensors 146, and/or other type of sensors. A medium collection reservoir agitation system 150 is also electrically connected to the controller 102. The medium collection reservoir agitation system 150 may include one or more motors 152 and/or one or more sensors 154.

A nutrient dispensement system 160 is shown. The nutrient dispensement system may include one or more valves 162 and/or one or more sensors 164 used to control dispensement of nutrients used to re-condition the medium.

In operation, the controller 102 may be configured via hardware and/or software to control fluid flow throughout the loops based on settings established by a user and based on the status of the processes within the bioreactor and the medium collection reservoir. For example, within the medium collection reservoir, medium adjustment may be performed in an automated manner, based on previously calculated metabolic and synthetic depletion rates, as well as real-time feedback obtained from a plurality of sensors.

Figure 4:
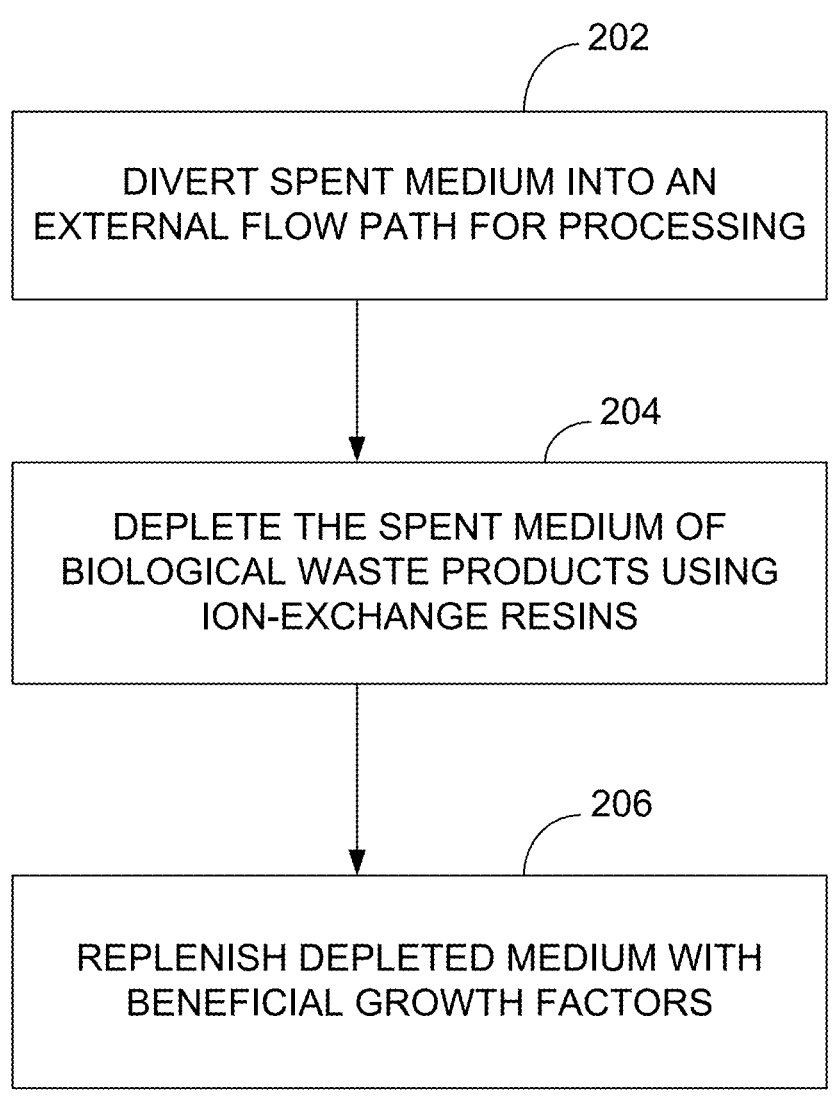
FIG. 4 illustrates one example of a method.

FIG. 4 illustrates one example of a method. In step 202, the method may divert spent medium into an external flow path for processing. Stirred-tank bioreactors primarily comprise a single, isolated chamber in which a suspension culture of cells is continuously agitated by a centrally situated impeller. A secondary, external flow path may be used which can be opened and closed autonomously, and through which fluid flow is driven by a pump. Cells which run through this external flow path may be separated from the medium and returned to the bioreactor via separation using tangential flow filters, microfluidics, or other separation methods, while the cell-free medium may be diverted into a tertiary flow path for medium processing, such as waste removal, and recycling.

In step 204, the spent medium may be depleted of biological waste products using ion-exchange resins. Medium diverted through the tertiary flow path may be diverted through a series of cartridges containing ion-exchange resins before accumulating in a collection reservoir for reconditioning. Ion-exchange resins have been demonstrated to be effective in minimizing levels of toxic chemicals in landfill wastewater runoff. These ion-exchange surfaces utilize charge-charge interactions to remove polar compounds from aqueous solutions, including metals and inhibitory byproducts of cell culture, such as ammonia and lactate. Previous studies have been conducted on the practicality of using ion-exchange resins and membranes in the context of binding excess metals and waste products of cell culture, however here, an impeller-driven closed-system bioreactor with a recirculation component is provided to thereby separate out recirculating cells and remove waste products without necessitating partial or complete medium exchanges.

In step 206, the depleted medium is replenished with beneficial growth factors. Beneficial factors are removed from culture medium as both a normal byproduct of cell culture, and as a side effect of exposure to ion-exchange resins. After the media has been diverted through both ion-exchange resin cartridges, it may accumulate in a secondary collection reservoir. Medium in this reservoir may be adjusted back to optimal conditions through targeted component delivery. Targeted supplementation can be achieved with any fluidic handling method, such as syringe pumps, peristaltic pumps, micropipettes, or other similar methods of low-volume (<10 mL) fluid handling. Of course, depending on scale, greater volumes may be present. Medium adjustment may be performed in an automated manner, based on previously calculated metabolic and synthetic depletion rates, as well as real-time feedback obtained from an array of biosensors. Adjusted parameters include, but are not limited to, pH, temperature, osmolality, and growth factor concentration. After replenishment, the medium may be pumped back into the primary cell culture reservoir to continue the cell culture process.

The invention is not to be limited to the particular embodiments described herein. In particular, the invention contemplates numerous variations in the type of cells being cultured, the type of bioreactor, the particular types of sensors used, the manner in which fluid control is performed, the manner in which separation of cells from medium occurs, the manner in which waste is removed from spent medium, the manner in which spent media is replenished, and other variations, options, and alternatives. The foregoing description has been presented for purposes of illustration and description. It is not intended to be an exhaustive list or limit any of the invention to the precise forms disclosed. It is contemplated that other alternatives or exemplary aspects are considered included in the invention. The description is merely examples of embodiments, processes or methods of the invention. It is understood that any other modifications, substitutions, and/or additions can be made, which are within the intended spirit and scope of the invention.

What is claimed is:

1. A method comprising:
   directing flow of a fluid from a bioreactor to an external path of a re-circulation loop, the fluid comprising a medium;
   separating cells from the medium to provide separated cells and returning the separated cells to the bioreactor thereby leaving spent medium;
   directing the spent medium through a downstream flow path that is separate from a cell return flow path;
   depleting the spent medium of biological waste products by passing the spent medium through a series of ion-exchange resins including an anion-exchange resin and a cation-exchange resin;
   accumulating the depleted spent medium in a medium collection reservoir:
   monitoring one or more properties of the depleted spent medium in the medium collection reservoir using one or more sensors;
   replenishing the depleted spent medium in the medium collection reservoir with beneficial growth factors based on measurements obtained from the one or more sensors monitoring the one or more properties of the depleted spent medium in the medium collection reservoir to thereby provide replenished medium;
   directing the replenished medium back to the bioreactor to thereby complete the re-circulation loop such that recycling of the medium occurs.

2. The method of claim 1 wherein the replenishing the depleted spent medium in the medium collection reservoir is performed automatically under control of a controls system based on measurements obtained from the one or more sensors.

3. The method of claim 1 further comprising monitoring the depleted spent medium within the medium collection reservoir including temperature of the depleted spent medium within the medium collection reservoir and pH of the depleted spent medium within the medium collection reservoir.

4. The method of claim 3 wherein a control system receives data generated from the monitoring the depleted spent medium within the medium collection reservoir and wherein the control system determines quantities of the beneficial growth factor to add to the medium collection reservoir.

5. The method of claim 1 wherein the depleting the spent medium of biological waste products comprise passing the spent medium through the anion-exchange resin and then through the cation-exchange resin.

6. The method of claim 1 wherein the separating the cells from the medium is performed using a separation system comprising at least one of filters and a microfluidic device.

7. The method of claim 1 wherein a control system controls the directing fluid flow from the bioreactor to the external path of the re-circulation loop.

8. The method of claim 1 wherein the separating cells is performed in-line.

9. A system comprising:

a bioreactor comprising a reaction chamber, an agitation system, an output line and a return line;

an in-line separation system to separate cells from medium fluidly connected to the output line from the bioreactor to thereby leave spent medium;

a biological waste removal system for depleting the spent medium of biological waste materials, wherein the biological waste removal system comprises a series of ion-exchange resins including an anion-exchange resin and a cation-exchange resin; and a medium collection reservoir fluidly connected to an output from the biological waste removal system, wherein the medium collection reservoir comprises an agitation system including an impeller.

10. The system of claim 9 wherein the bioreactor, in-line separation system, biological waste removal system, and medium collection reservoir are arranged to provide a self-contained closed-system recirculation loop.

11. The system of claim 9 further comprising a control system for monitoring and/or control of the system.

12. The system of claim 11 further comprising a first plurality of sensors associated with the bioreactor and operatively connected to the control system.

13. The system of claim 12 further comprising a second plurality of sensors associated with the medium collection reservoir and operatively connected to the control system.

14. The system of claim 9 wherein the in-line separation system comprises filters.

15. The system of claim 9 wherein the in-line separation system comprises microfluidics configured for separation.

16. The system of claim 9 wherein the biological waste removal system comprises a plurality of replaceable ion-exchange resin cartridges.

17. The system of claim 9 wherein the agitation system is configured to mix the depleted spent medium during replenishment of beneficial growth factors.

* * * * *